United States Patent [19]

Bakker et al.

[11] 4,175,092
[45] Nov. 20, 1979

[54] EXTRACTION PROCESS

[75] Inventors: Pieter M. Bakker; Cornelis E. Kind, both of Amsterdam, Netherlands

[73] Assignee: Shell Oil Company, Houston, Tex.

[21] Appl. No.: 959,958

[22] Filed: Nov. 13, 1978

Related U.S. Application Data

[63] Continuation-in-part of Ser. No. 856,811, Nov. 30, 1977, abandoned.

[30] Foreign Application Priority Data

Nov. 30, 1976 [GB] United Kingdom ............ 49831/76

[51] Int. Cl.² .................. C07C 141/04; C07C 143/02
[52] U.S. Cl. .......................... 260/456 R; 260/459 R; 260/460; 260/513 R; 568/918
[58] Field of Search ............... 260/456 R, 459 R, 460, 260/513 R; 568/918

[56] References Cited

U.S. PATENT DOCUMENTS

| 2,078,638 | 4/1937 | Rulrutz | 260/459 R |
| 2,152,163 | 3/1939 | Tulleners | 260/459 R |
| 2,196,177 | 4/1940 | Burk et al. | 568/918 |
| 2,522,212 | 9/1950 | Pammers | 260/459 R |

FOREIGN PATENT DOCUMENTS

| 931211 | 7/1963 | United Kingdom | 568/918 |
| 991123 | 5/1965 | United Kingdom | 568/918 |

Primary Examiner—Norman Morgenstern

[57] ABSTRACT

Non-surface active organic material is recovered from an aqueous-based mixture comprising water, sulphated or sulphonated organic matter and non-surface active organic material by extracting said mixture with a $C_6$ ketone or a $C_1$ to $C_6$ alkyl acetate as the sole extraction solvent thereby forming a ketone or acetate extract phase containing essentially all of the non-surface active organic matter and a raffinate phase containing water, some of the ketone or acetate solvent and essentially all of the sulphated or sulphonated organic matter, said extract phase being subsequently separated into a ketone or acetate solvent fraction and a non-surface active organic material fraction.

10 Claims, 1 Drawing Figure

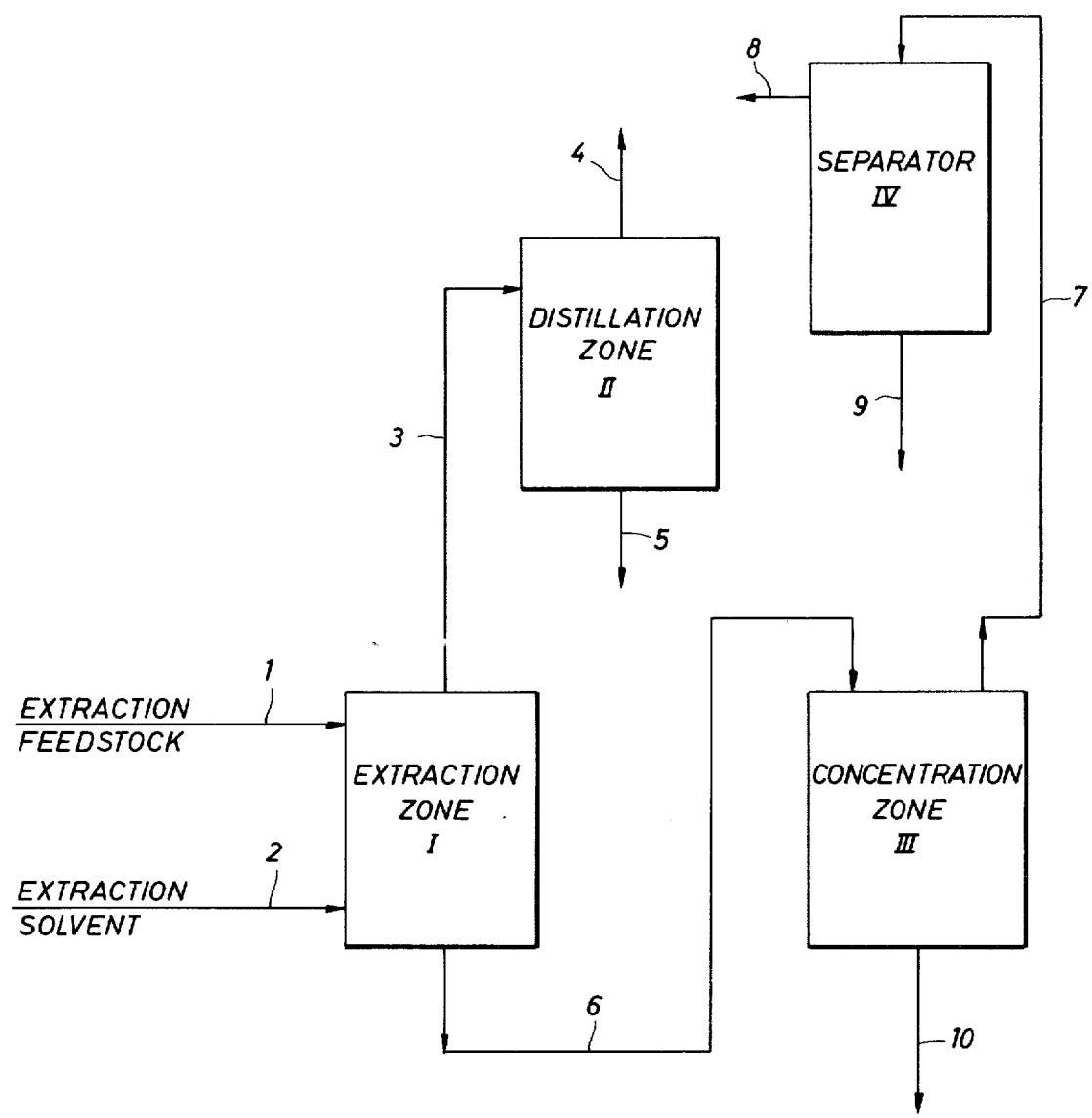

EXTRACTION PROCESS

This application is a continuation-in-part of copending application Ser. No. 856,811, filed Nov. 30, 1977 now abandoned.

BACKGROUND OF THE INVENTION

The present invention relates to the extraction of non-surface active organic material from aqueous anionic surfactant solutions. Processes for the preparation of anionic detergents usually result in production of a mixture comprising water/anionic detergent/non-surface active organic material. It is desirable to remove the non-surface active organic material from the detergent product and this may be achieved in several ways, one of which is by the extraction thereof with suitable solvents.

One important class of anionic detergents includes those obtained by the sulphation or sulphonation or organic material. Examples include alkyl sulphates, alkyl sulphonates and alkenyl sulphonates. Such anionic detergents are suitably prepared by reacting $C_8$ to $C_{22}$ olefins or alcohols with sulphuric acid or sulphur trioxide or by reacting paraffins with sulphur dioxide and oxygen to form the corresponding sulphuric or sulphonic acids followed by neutralizing such acids with bases to form the corresponding salts which are anionic detergents. The principal products of such processes are aqueous solutions of sulphated or sulphonated organic matter. However, these products also contain organic material which is not surface active. Such non-surface active organic material may be unreacted starting material and/or may be formed during the process. Examples of this non-surface active organic material include $C_8$ to $C_{22}$ paraffins, olefins, and alcohols as well as various by-products such as polymers and sultones. This non-surface active organic material may also be described as unconverted organic matter.

In conventional practice, the above described non-surface active organic material is usually removed from the aqueous anionic detergent product by extraction with hydrocarbon solvents. The extraction usually takes place after neutralization since further amounts of non-surface active organic material may be formed during the neutralization reaction. One problem attributable to the use of hydrocarbons as sole extractants is that there is then a strong tendency toward formation of undesirable emulsions or gels. The emulsion formation may be avoided by carrying out the extraction in the presence of various oxygen-containing compounds such as low molecular weight alcohols, e.g. isopropyl alcohol (IPA), and ketones (see British Pat. No. 480,904; British Pat. No. 726,994). Thus insofar as gasoline/IPA extractions are concerned, the products are a gasoline/IPA/non-surface active organic material extract and a gasoline/IPA/water/ sulphated or sulphonated organic matter raffinate. The solvents may be separated, recovered and reused in further extractions. However, with the use of two solvents for extraction it is necessary to provide separate solvent recovery systems for each, a requirement which adds to the total capital and operating costs of a commercial extraction unit.

SUMMARY OF THE INVENTION

It has now been found that ketones containing six carbon atoms, in particular methyl isobutyl ketone, or certain alkyl acetates in which the alkyl grouping contains one to six carbon atoms, in particular methyl, ethyl and isopropyl acetates, may be used as the sole extractant for the extraction of non-surface active organic material from a mixed extraction feedstock comprising water, sulphated or sulphonated organic matter and non-surface active organic material, which is obtained through the sulphation or sulphonation of $C_8$ to $C_{22}$ olefins, paraffins or alcohols to produce the corresponding sulphuric or sulphonic acids followed by neutralization of these acids with base. Such ketones and acetates are very effective extractants for the non-surface active organic material in the resulting neutralized reaction mixture. Furthermore, in this extraction process, the ketones and acetates do not contribute to the formation of emulsions, are thermally stable, and may easily be recovered from the extract and raffinate. The use of such ketones or acetates as sole extractants has the further advantage that only a single solvent has to be separated and recovered from the extract and the raffinate.

Accordingly, the instant invention is concerned with a process for separating non-surface active organic material from a mixed extraction feedstock containing water, sulphated or sulphonated organic matter and non-surface active organic material which comprises extracting said feedstock with a solvent selected from the class consisting of a $C_6$ ketone and an alkyl acetate having a $C_1$ to $C_6$ alkyl substituent, as the sole extraction solvent, thereby forming a ketone or acetate extract phase containing essentially all of the non-surface active organic matter and a raffinate phase containing water, some ketone or acetate solvent and essentially all of the sulphated or sulphonated organic matter, said extract phase being subsequently separated into a ketone or acetate solvent fraction and a non-surface active organic material fraction. When a $C_6$ ketone is employed as the sole extraction solvent in accordance with the invention, it is preferred that the temperature during extraction be maintained at less than 60° C. to avoid a tendency at higher temperatures for the ketone to dissolve into the extract phase, both the sulphated or sulphonated organic matter and the non-surface active organic matter, and thus to lose its effectiveness as an extraction solvent.

DESCRIPTION OF THE PREFERRED EMBODIMENTS

Suitable extraction feedstocks for the process of the instant invention comprise sulphated or sulphonated surface active organic matter produced by reacting $C_8$ to $C_{22}$ olefins or alcohols with sulphuric acid or sulphur trioxide or by reacting paraffins with sulphur dioxide and oxygen to form the corresponding sulphuric or sulphonic acids, followed by the neutralization of such acids with bases to form the corresponding salts. Examples of such surface active organic salts include alkyl sulphates, alkyl sulphonates, and alkenyl sulphonates. The feedstocks also contain non-surface active organic material, which may be unreacted starting material from the sulphation or sulphonation and subsequent neutralization reaction process and/or may be by-products formed during that process. Examples of such non-surface active organic material include $C_8$ to $C_{22}$ paraffins, olefins, and alcohols, as well as by-products such as polymers and sultones. Suitable feedstocks comprise aqueous mixtures containing non-surface active organic material and sulphated or sulphonated organic matter in weight ratios of from 1:10 to 10:1, preferably of from 0.25:1 to 2.5:1. To effect good separation of the mixed extraction feedstock into the desired extract and raffinate phases, it is preferred that the extraction feedstock contain at least 200 percent by weight (%w), more preferably from 300 to 1000%w, of water, based on the weight of sulphated or sulphonated organic matter in the feedstock.

The feedstock may also contain inorganic salts, e.g. alkali, alkaline-earth, or ammonium sulphate, produced by neutralization of inorganic acid not recovered from the sulphated or sulphonated organic matter prior to the neutralization step. The amount of such salts may be from 2.5 to 100%w, based on the weight of sulphated or sulphonated organic matter, but is usually from 5 to 20%w.

According to the process of the instant invention, this feedstock is contacted, preferably in counterflow, with from 20 to 500%w, preferably from 75 to 200%w, of a $C_6$ ketone or a $C_1$ to $C_6$ alkyl acetate, based on the weight of extraction feedstock. A particularly suitable $C_6$ ketone is methyl isobutyl ketone and particularly suitable acetates are methyl, ethyl and isopropyl acetates. It is important, especially insofar as the use of methyl isobutyl ketone is concerned, to carry out the extraction at an appropriate temperature and dilution, since at high temperatures, high concentrations of the sulphated or sulphonated organic matter and high concentrations of inorganic salts, there is an increasing tendency for the methyl isobutyl ketone to dissolve both the sulphated or sulphonated organic matter and the non-surface active organic material which necessitates a further extraction step to extract the sulphated or sulphonated organic matter from the non-surface active matter. (See British Pat. No. 480,940 which proposes the use of certain ketones for desalting hot feedstocks and then the extraction of the desalted feedstock with gasoline). Suitably the extraction with ketone solvent is carried out at a temperature of below 60° C., preferably below 50° C., and most preferably at ambient temperature. Since it is difficult to completely separate the sulphated or sulphonated organic matter from the non-surface active organic material without using a very high number of theoretical extraction stages, the raffinate may suitably contain small amounts, usually less than 5%w, of non-surface active organic material, based on the weight of sulphated or sulphonated organic matter in the raffinate.

The ketone or acetate solvent is distributed during the extraction into both the extract and raffinate phases in proportions dependent upon such factors as the composition of the extraction feedstock, the relative quantities of feedstock and solvent, and the extraction temperature. It will be appreciated by one skilled in the art that such factors will vary according to the numerous applications that may be made of the invention. However, in order to minimize removal of solvent and water from the raffinate phase subsequent to the extraction, it is preferred that the invention be practiced so that the extract phase contains more than 60% of the ketone or acetate solvent and the raffinate phase contains no more than 40% of the solvent.

The extraction apparatus used to effect the necessary contact between solvent and extraction feedstock so as to yield the extract and raffinate phases according to the process of the invention may be of conventional design. Commonly, a vertical column equipped with appropriate packing or perforated trays to aid in contacting the solvent and feedstock in countercurrent flow is used for such an extraction.

The raffinate as obtained by the process of the present invention may be used as an anionic detergent, or it may be concentrated, e.g. by distillation or partial evaporation, to remove the residual ketone or acetate and a part of the water therefrom.

The present invention is particularly suitable for recovering non-surface active organic material from feedstocks obtained by sulphating $C_8$ to $C_{22}$ olefins, which may be internal or alpha-olefins, with a stoichiometric excess of sulphuric acid, based on olefin, said sulphuric acid suitably having a concentration of from 75 to 100%w. The olefins may be sulphated in the presence of at least 15% mole of alcohol on olefin as described in our commonly assigned copending application, Ser. No. 856,141, filed Nov. 28, 1977. The resulting alkyl sulphuric acids may then be subjected to extraction. However, it is preferred that they are first converted to the corresponding salts by neutralization with bases such as aqueous amines or such as aqueous ammonium, alkalimetal or alkaline earth metal hydroxides, carbonates or bicarbonates. The sulphation/neutralization reaction process of the copending application also includes a step for the partial or substantially complete removal of unconverted sulphuric acid, e.g. by de-acidification, i.e. removal of the unconverted acid itself, or by de-salting, i.e. removal of the acid in the form of an inorganic sulphate thereof, prior to subjecting the reaction process effluent mixture to the extraction process of the instant invention. The non-surface active organic material present in the product of this process comprises mainly unreacted $C_8$ to $C_{22}$ olefins and secondary $C_8$ to $C_{22}$ alcohols. Such alcohols may be formed in the process and/or be present in the sulphation reaction feedstock, passing unreacted through the sulphation and neutralization reaction zones. When the extraction process of the instant invention is carried out upon the extraction feedstock obtained in this manner, the aqueous extraction feedstock suitably contains secondary $C_8$ to $C_{22}$ alcohols and $C_8$ to $C_{22}$ olefins in weight ratios of from 5:1 to 20:1, preferably from 7:1 to 15:1 in addition to the sulphated organic matter. Various polymeric by-products may also be present. Moreover since it is very difficult to remove all of the unreacted sulphuric acid by de-acidification and/or by de-salting, the feedstock may also contain variable amounts of inorganic sulphates. For example, sodium sulphate may be present when sodium hydroxide is the base in the neutralization reaction. Usually the amount of such inorganic sulphates is at least 2.5%w, most commonly from 5 to 20%w, based on the weight of the salts of $C_8$ to $C_{22}$ monoalkyl sulphuric acids present. These inorganic salts appear in the raffinate phase following extraction.

Consequently, the preferred feedstock for use in the present invention is that obtained by sulphating one or more $C_8$ to $C_{22}$ olefins, optionally in the presence of one or more secondary $C_8$ to $C_{22}$ alcohols, with sulphuric acid and neutralizing the organic acids so formed to prepare the salts thereof with the sulphation reaction product being de-acidified and/or the subsequent neutralization reaction product being de-salted before the feedstock is extracted with the ketone or acetate. In this preferred aspect of the invention, a mixture of $C_8$ to $C_{22}$ olefins and secondary $C_8$ to $C_{22}$ alcohols is separated from the sulphation reaction product mixture comprising water, salts of $C_8$ to $C_{22}$ monoalkyl sulphuric acids, inorganic sulphates and the mixture of $C_8$ to $C_{22}$ olefins and secondary $C_8$ to $C_{22}$ alcohols by extracting the reaction product mixture with a solvent selected from the class consisting of a $C_6$ ketone and an alkyl acetate having a $C_1$ to $C_6$ alkyl substituent thereby forming a ketone or acetate extract phase containing essentially all of the mixture of $C_8$ to $C_{22}$ olefins and secondary $C_8$ to $C_{22}$ alcohols and a raffinate phase containing water, some of the ketone or acetate solvent and essentially all of the salts of $C_8$ to $C_{22}$ monoalkyl sulphuric acids and the inorganic sulphates, said extract phase being subsequently separated into a ketone or acetate solvent fraction and a fraction containing the $C_8$ to $C_{22}$ olefins and secondary $C_8$ to $C_{22}$ alcohols.

The $C_8$ to $C_{22}$ olefins/secondary $C_8$ to $C_{22}$ alcohols fraction, alternatively described as the non-surface active organic material fraction, which may also contain small amounts of polymeric by-products, may be recycled to the sulphation reaction.

The invention will now be illustrated by reference to the accompanying drawing which is a schematic diagram of a process according to the present invention.

The extraction feedstock comprising water, sulphated or sulphonated organic matter, and non-surface active organic material is fed via line 1 to an extraction zone I where it is treated in counterflow with the ketone or acetate extraction solvent introduced by line 2 to yield the extract phase taken overhead by line 3 and the raffinate phase removed as bottoms product by line 6. The extract in line 3, comprising ketone or acetate solvent and essentially all of the non-surface active organic material is fed to a distillation zone II where it is separated into the overhead ketone or acetate fraction of line 4 which may be recycled to the extraction zone I and the residual non-surface active organic material fraction of line 5 which may be recycled to a sulphation or sulphonation reaction zone (not shown). The raffinate phase in line 6 comprising water, some of the ketone or acetate solvent and essentially all of the sulphated or sulphonated organic matter may be used as an anionic detergent or it may be concentrated by partial evaporation or distillation in zone III to yield an aqueous ketone or acetate fraction taken overhead by line 7 and a bottoms product in line 10 containing the sulphated or sulphonated organic matter and residual water. The overhead fraction may be passed via line 7 to a separator IV where it is separated into the ketone or acetate fraction of line 8 and the water fraction of line 9. This concentrated ketone or acetate fraction in line 8 may also be recycled to the extraction zone I.

The invention will now be illustrated by reference to the following Examples.

EXAMPLE I

The extraction feedstock used was obtained by sulphation of a $C_{14}$ alpha-olefin with sulphuric acid in the presence of a secondary $C_{15}$ alcohol, followed by deacidification and neutralization with NaOH. The feedstock had the following composition:

|  | parts by weight |
|---|---|
| water | 4885 |
| Na salt of $C_{14}/C_{15}$ secondary alkyl sulphuric acid | 1000 |
| $C_{14}$ olefins | 69 |
| $C_{14}/C_{15}$ secondary alcohol | 759 |
| $Na_2SO_4$ | 103 |

The extraction feedstock was contacted in a column comprising approximately 4 theoretical extraction stages, at ambient temperature, in counterflow, with 147%w, on feedstock, of methyl isobutyl ketone (MIBK). The extract phase obtained had the composition:

|  | parts by weight |
|---|---|
| MIBK | 7570 |
| $C_{14}$ olefin | } 823 |
| $C_{14}/C_{15}$ secondary alcohol | |

The raffinate phase obtained had the composition:

|  | parts by weight |
|---|---|
| MIBK | 2440 |
| water | 4845 |
| Na salt of $C_{14}/C_{15}$ sec. alkyl sulphuric acid | 1000 |
| $Na_2SO_4$ | 103 |
| $C_{14}$ olefin | } 5 |
| $C_{14}/C_{15}$ secondary alcohol | |

The extract phase was distilled to separate the MIBK as the overhead fraction.

The raffinate phase was partially evaporated to remove all the MIBK and 3447 parts by weight of the water therefrom.

EXAMPLE II

The procedure of Example I was repeated with the exception that ethyl acetate (142%w on feedstock) was used as the extractant. The extract phase obtained had the composition:

|  | parts by weight |
|---|---|
| ethyl acetate | 7414 |
| $C_{14}$ olefin | } 821 |
| $C_{14}/C_{15}$ secondary alcohol | |

The raffinate phase obtained had the composition:

|  | parts by weight |
|---|---|
| ethyl acetate | 2280 |
| water | 4845 |
| Na salt of $C_{14}$ $C_{15}$ sec. alkyl sulphuric acid | 1000 |
| $Na_2SO_4$ | 103 |
| $C_{14}$ olefin | } 7 |
| $C_{14}/C_{15}$ secondary alcohol | |

EXAMPLE III

The procedure of Example I was repeated with the exception that isopropyl acetate (138%w on feedstock) was used as the extractant. The extract phase obtained had the composition:

|  | parts by weight |
|---|---|
| isopropyl acetate | 7254 |
| $C_{14}$ olefin | } |

-continued

| | parts by weight |
|---|---|
| $C_{14}/C_{15}$ secondary alcohol | 821 |

The raffinate phase obtained had the composition:

| | parts by weight |
|---|---|
| isopropyl acetate | 2120 |
| water | 4845 |
| Na salt of $C_{14}/C_{15}$ sec. alkyl sulphuric acid | 1000 |
| $Na_2SO_4$ | 103 |
| $C_{14}$ olefin } | 7 |
| $C_{14}/C_{15}$ secondary alcohol } | |

As stated heretofore, the non-surface active organic material may be recycled to the sulfation or sulfonation reaction zone. While recycle is obviously desirable in order to maximize the utilization of olefins, paraffins, and alcohols capable of undergoing sulfation or sulfonation, it is recognized in the art that such recycle is often subject to certain constraints and conditions. With regard to several of the particular components commonly found in sulfation or sulfonation reaction mixtures and in the non-surface active materials recovered therefrom, there are teachings in the art illustrating their removal from recycle streams and/or their conversion into substances more suitable for recycle. For example, although the aforementioned co-pending application relating to sulfation of olefins recommends generally that the whole of the recovered non-surface active material be recycled and specifically that alcohol by-products be continuously recycled in large quantity, the prior art, as evidenced by U.S. Pat. No. 2,640,070, has placed limitations on the quantity of alcohol added to the olefin sulfation reaction. As a result of these limitations, excess alcohol is generally not directly recycled but instead is disposed of, for instance, by catalytic dehydrogenation back to the olefin (British Pat. No. 656,064). Likewise, it has been a common practice in the art to remove polymeric by-products from sulfation or sulfonation reaction mixtures as a stream separate and distinct from that intended for recycle. The separated polymer may be disposed of, or it can be subsequently sulfated in a secondary sulfation reactor to yield surface-active material. (Netherlands Pat. No. 86,626). It is intended that recycle of non-surface active material practiced in conjunction with the extraction process of the instant invention be interpreted in accordance with such teachings of the relevant prior art. Consequently, recycle may suitably be in whole or in part and may incorporate processing steps in addition to the mere transport of material to the reaction zone.

What is claimed is:

1. A process for recovering non-surface active material from an aqueous based mixture containing water, surface active organic salts comprising sulphated or sulphonated organic matter, and non-surface active organic material, said mixture being obtained by the sulphation or sulphonation of $C_8$ to $C_{22}$ olefins, paraffins or alcohols to yield the corresponding monoalkyl sulphuric or sulphonic acids followed by neutralization of said acids with a base to afford the corresponding surface active organic salts, which comprises extracting the aqueous-based mixture with, as sole solvent, a $C_6$ ketone, at a temperature of below 60° C., or an alkyl acetate in which the alkyl grouping contains one to six carbon atoms to form a ketone or alkyl acetate based extract phase containing essentially all of the non-surface active organic matter and a raffinate phase containing water, some of the ketone or acetate solvent and essentially all of the sulphated or sulphonated organic matter, and subsequently separating the extract phase into a ketone or acetate fraction and a non-surface active organic material fraction which is recycled to the sulphation or sulphonation reaction.

2. The process of claim 1, wherein the extraction solvent is selected from a group consisting of methyl isobutyl ketone, ethyl acetate, and isopropyl acetate.

3. The process of claim 2, wherein the extraction feedstock contains from 300 to 1000%w of water, based on the weight of the sulphated or sulphonated organic material in the feedstock.

4. The process of claim 3, wherein the amount of sulphated or sulphonated organic matter in the extraction feedstock is from 5 to 25%w, based on the weight of the feedstock.

5. The process of claim 4, wherein the weight ratio of the non-surface active organic material to the sulphated or sulphonated organic matter in the extraction feedstock is from 0.25:1 to 2.5:1.

6. The process of claim 5, wherein the extraction feedstock also contains an inorganic sulphate in an amount of from 5 to 20%w, based on the weight of sulphated or sulphonated organic matter in the feedstock.

7. The process of claim 6, wherein the sulphated or sulphonated organic matter is one or more salts of $C_8$ to $C_{22}$ monoalkyl sulphuric acids.

8. The process of claim 7, wherein the non-surface active organic material is a mixture consisting essentially of one or more $C_8$ to $C_{22}$ olefins and one or more secondary $C_8$ to $C_{22}$ alcohols.

9. The process of claim 8, wherein the weight ratio of the secondary $C_8$ to $C_{22}$ alcohol to the $C_8$ to $C_{22}$ olefin in the extraction feedstock is from 5:1 to 20:1.

10. The process of claim 9, wherein the extraction feedstock is extracted at a temperature of below 50° C.

* * * * *